US009494525B2

(12) United States Patent
Tarumi et al.

(10) Patent No.: US 9,494,525 B2
(45) Date of Patent: Nov. 15, 2016

(54) AUTOMATED ANALYZER AND AUTOMATED ANALYSIS METHOD

(71) Applicant: Hitachi High-Technologies Corporation, Minato-ku, Tokyo (JP)

(72) Inventors: Shinji Tarumi, Tokyo (JP); Chie Yabutani, Tokyo (JP); Akihisa Makino, Tokyo (JP); Chihiro Manri, Tokyo (JP); Satoshi Mitsuyama, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/646,150

(22) PCT Filed: Nov. 5, 2013

(86) PCT No.: PCT/JP2013/079835
§ 371 (c)(1),
(2) Date: May 20, 2015

(87) PCT Pub. No.: WO2014/080751
PCT Pub. Date: May 30, 2014

(65) Prior Publication Data
US 2015/0316531 A1 Nov. 5, 2015

(30) Foreign Application Priority Data
Nov. 26, 2012 (JP) ................................ 2012-257473

(51) Int. Cl.
*G06F 19/00* (2011.01)
*G01N 33/86* (2006.01)
(Continued)

(52) U.S. Cl.
CPC .............. *G01N 21/82* (2013.01); *G01N 21/17* (2013.01); *G01N 21/272* (2013.01); *G01N 33/49* (2013.01);
(Continued)

(58) Field of Classification Search
CPC ...................... G01N 33/86; G01N 2035/00702; G01N 2035/0097; G01N 2015/1402;
(Continued)

(56) References Cited

U.S. PATENT DOCUMENTS 4,720,787 A   1/1988   Lipscomb
6,438,499 B1  8/2002   Hayashi
(Continued)

FOREIGN PATENT DOCUMENTS

CN   102428373 A   4/2012
CN   102741680 A   10/2012
(Continued)

OTHER PUBLICATIONS

International Search Report (PCT/ISA/210) dated Feb. 4, 2014 with English translation (five pages).
(Continued)

*Primary Examiner* — Lyle Alexander
*Assistant Examiner* — Jennifer Wecker
(74) *Attorney, Agent, or Firm* — Crowell & Moring LLP

(57) ABSTRACT

Provided is technology for blood clotting reactions capable of analyzing a blood clotting reaction with a high degree of precision, by precisely detecting and removing noise, regardless of the location where the noise is generated in the light intensity data. This automated analyzer approximates, with an approximation curve, time series data for transmitted light intensity or scattered light intensity of light emitted onto a sample, and, in this process, removes abnormal data points that deviate from the approximation curve (see FIG. 2).

13 Claims, 9 Drawing Sheets

(51) Int. Cl.
*G01N 33/49* (2006.01)
*G01N 21/17* (2006.01)
*G01N 35/00* (2006.01)
*G01N 21/27* (2006.01)
*G01N 21/82* (2006.01)
*G01N 33/53* (2006.01)
*G01N 21/25* (2006.01)
*G01N 21/51* (2006.01)
*G01N 21/59* (2006.01)
*G01N 30/86* (2006.01)
*G01N 35/04* (2006.01)

(52) U.S. Cl.
CPC .......... *G01N 33/4905* (2013.01); *G01N 35/00* (2013.01); *G01N 35/00584* (2013.01); *G01N 21/25* (2013.01); *G01N 21/27* (2013.01); *G01N 30/8693* (2013.01); *G01N 33/53* (2013.01); *G01N 33/86* (2013.01); *G01N 2021/513* (2013.01); *G01N 2021/5961* (2013.01); *G01N 2035/0097* (2013.01); *G01N 2035/00425* (2013.01); *G01N 2035/00702* (2013.01); *G01N 2035/0453* (2013.01); *G06F 19/00* (2013.01); *G06F 19/321* (2013.01)

(58) Field of Classification Search
CPC .................. G01N 2021/5961; G01N 30/8693; G01N 2021/513; G01N 2035/00425; G01N 2035/0453; G01N 21/17; G01N 21/272; G01N 21/82; G01N 33/49; G01N 33/4905; G01N 35/00; G01N 35/005; G06F 19/321; G06F 19/702
See application file for complete search history.

(56) References Cited

U.S. PATENT DOCUMENTS

| | | | |
|---|---|---|---|
| 2012/0064636 | A1 | 3/2012 | Mitsuyama et al. |
| 2012/0282139 | A1* | 11/2012 | Makino .................. G01N 21/51 422/73 |
| 2012/0288409 | A1 | 11/2012 | Inabe et al. |
| 2013/0122596 | A1* | 5/2013 | Kamihara .......... B01F 11/0266 436/43 |

FOREIGN PATENT DOCUMENTS

| | | |
|---|---|---|
| EP | 0 932 041 A2 | 7/1999 |
| EP | 2 434 292 A1 | 3/2012 |
| JP | 7-82020 B2 | 9/1995 |
| JP | 2000-88832 A | 3/2000 |
| JP | 2000-131284 A | 5/2000 |
| JP | 2004-347385 A | 12/2004 |
| JP | 2006-337125 A | 12/2006 |
| JP | 2007-323440 A | 12/2007 |
| JP | 2008-209350 A | 9/2008 |
| WO | WO 2011/021198 A2 | 2/2011 |
| WO | WO 2012/008324 A1 | 1/2012 |

OTHER PUBLICATIONS

Japanese-language Written Opinion (PCT/ISA/237) dated Feb. 4, 2014 (three pages).
Chinese Office Action issued in counterpart Chinese Application No. 201380060805.9 dated Jan. 29, 2016 (four (4) pages).
European Search Report issued in counterpart European Application No. 13856862.1 dated Jul. 18, 2016 (three pages).

* cited by examiner

AUTOMATED ANALYZER AND AUTOMATED ANALYSIS METHOD

TECHNICAL FIELD

The present invention relates to techniques for analyzing components included in blood-derived samples. In particular, the present invention relates to techniques for analyzing blood-clotting reactions.

BACKGROUND ART

Blood clotting test is performed for various purposes such as for identifying clinical conditions of coagulation fibrinolytic system, for diagnosing DIC (disseminated intravascular coagulation), for checking effects of thrombus treatments, or for diagnosing hemophilia. Conventionally, blood clotting test has been performed by visually identifying fibrin precipitation which is a final point of blood clotting reaction. However, after 1960's, blood clotting analysis devices which are developed for improving test throughputs and precisions have been used in usual tests.

In detecting fibrin precipitations by blood clotting analysis devices, methods such as electric resistance detection, optical detection, or mechanical methods are used, in particular, optical detection is a contactless method in which samples do not touch with foreign objects in clotting reactions. Thus optical detection is widely used. There are two types of optical detections; a transmitted light detection in which, variation of transmitted light, is measured when aggregated substances are generated in reaction containers; and a scattered light detection in which scattered light is detected. Both methods analyze the detected chronological light intensity to calculate clotting time. Various methods have been proposed so far.

In the technique described in Patent Literature 1 listed below: times T1 and T2, at which the most recently acquired signals become X-times and Y-times (0<X<Y<1) larger respectively, are searched by scanning from the most recently acquired signals toward the initially acquired signals; polynomial regression, analysis is performed with respect to the signals from the time T1 to the time T2; and the clotting time is calculated from the acquired approximated curve. Accordingly, the unevenness of data is removed, thereby attempting to accurately calculate the clotting time.

CITATION LIST

Patent Literature

Patent Literature 1: JP Patent (Koukoku) No. H07-82020 B2 (1995)

SUMMARY OF INVENTION

Technical Problem

Optical detection calculates the clotting time by analyzing chronological light intensities acquired from immediately after the reagent is mixed with the sample. However, during the reaction, especially immediately after the initiation of the reaction, it is highly likely that noises are included in the acquired light intensity and erroneous clotting, times may be calculated.

In Patent Literature 1 above, data before the time T1, which may include noises, is excluded from the test target and data within the range between the times T1 and T2 only is provided to the test, thereby attempting to solve the problem. However, if a noise occurs at a stage where aggregated substances are well generated, for example, the noise is included between the times T1 and T2. Accordingly, erroneous approximated curves and erroneous clotting times may be calculated.

The present invention is made in the light of the above-described technical problems. It is an objective of the present invention to provide a technique for precisely detecting and removing noises regardless of the locations where noises occur in the light intensity data, thereby analyzing blood clotting reactions with high precision.

Solution to Problem

An automated analysis device according to the present invention approximates, using an approximated curve, chronological data of transmitted light or of scattered light generated by light irradiated onto a sample. During that process, the automated analysis device removes abnormal data points that are departed from the approximated curve.

Advantageous Effects of Invention

With the automated analysis device according to the present invention, it is possible to precisely detect and remove noises occurring in measured data during blood clotting reactions, thereby analyzing blood clotting reactions with high precision.

Technical problems, configurations, and effects other than those mentioned above will be apparent with reference to the embodiments below.

BRIEF DESCRIPTION OF DRAWINGS

FIG. 13 is a diagram showing a condition after repeating detections and removals of noise data points and calculations of an approximated curve 340.

DESCRIPTION OF EMBODIMENTS

Embodiment 1

Device Configuration

Figure 1:
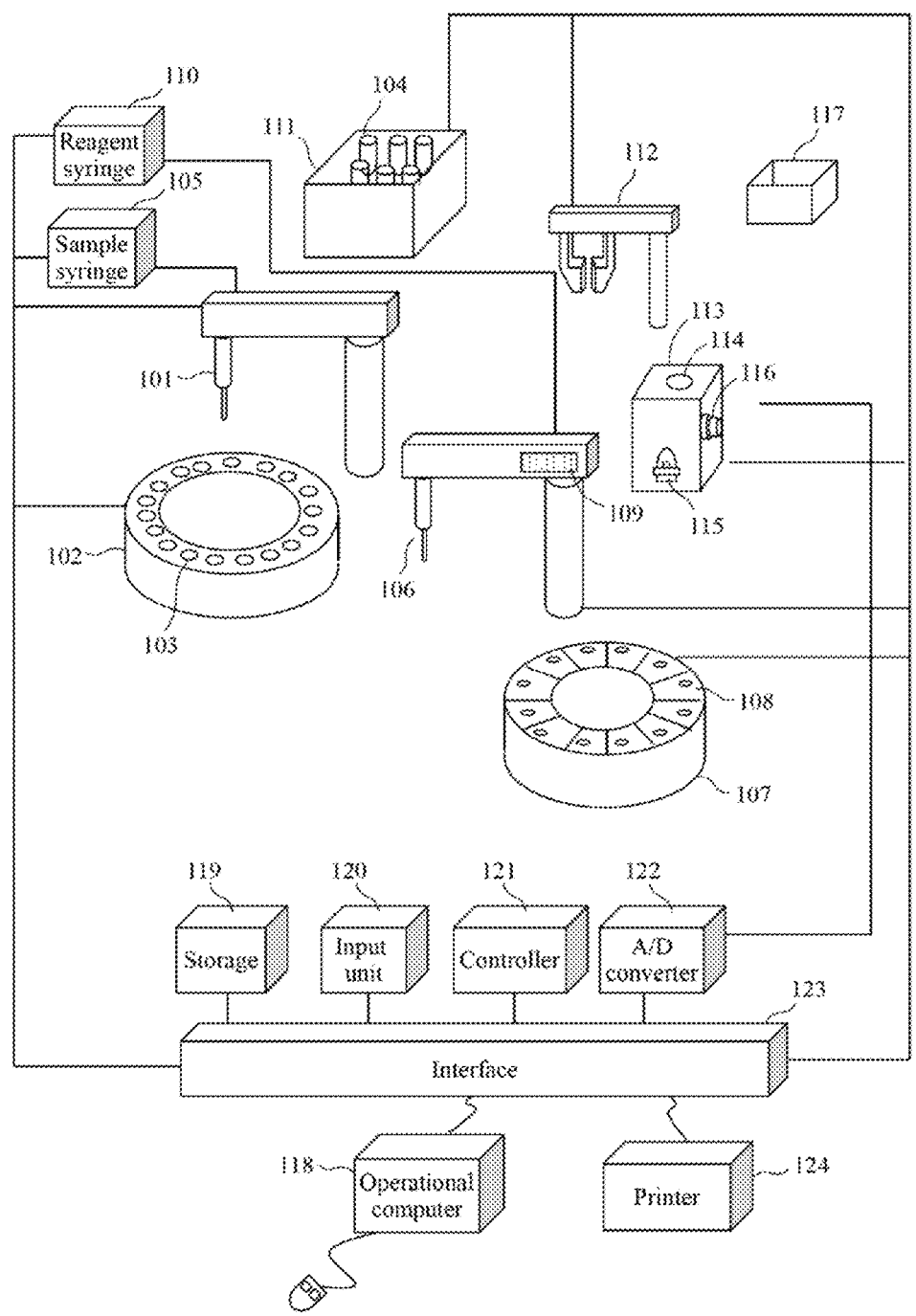
FIG. 1 is a configuration diagram of an automated analysis device according to an embodiment 1.

FIG. 1 is a configuration diagram of an automated analysis device according to an embodiment 1 of the present invention. Since functionalities of each of parts are commonly known, detailed descriptions will be omitted.

The automated analysis device according to the embodiment 1 is configured so that a sample in a sample container 103 located in a sample disc 102 rotating leftward or rightward is suctioned using a sample dispenser 101 and is discharged into a reaction container 104. The sample dispenser 101 performs suctioning actions and discharging actions along with actions of a sample syringe pump 105. A reagent dispenser 106 is configured to suction the sample in a sample container 108 located in a sample disc 107 and to discharge the sample into the sample container 104. The reagent dispenser 106 includes a reagent heater 109 within it. The reaction container 104 is held up from a reagent container stock 111 by a rotating reaction container carrier 112, is moved rotationally, and is located in a reagent container locator 114 in a detector 113. The reagent container locator 114 is provided with a recess so that the reagent container 104 may be placed on it. The reagent container 104 may be inserted into the recess. At least, one of the reagent container locator 114 and at least one of the detector 113 are provided. The reagent container carrier 112 carries and places the reagent container 104.

The measurement flow will be described below. Analysis items to be analyzed for each of the samples are inputted from an input unit 120 such as keyboards or from an operational computer 118. A controller 121 controls operations of the detector 113. The sample dispenser 101 suctions the sample in the sample container 103 located in the sample disc 102, and dispenses the sample into the reaction container 104 placed on the reaction container locator 114 in the detector 113. The reagent dispenser 106 suctions the reagent from the reagent container 108 located in the reagent disc 107. The reagent beater 109 heats the reagent up to an appropriate temperature. The reagent dispenser 106 dispenses the reagent into the reaction container 104. After the reagent is discharged, the blood clotting reaction begins immediately.

A light source 115 irradiates light onto the reaction container 104. A detector 116 detects, using such as photo diodes, scattered light or transmitted light caused by reactive solutions in the reaction container. The measured light signal is captured by the controller 121 as chronological light intensity data through an A/D converter 122 and through an interface 123. The controller 121 uses the light intensity data to calculate the clotting time. The calculated result is printed out by a printer 124 through the interface 123 or is outputted on a display of the operational computer 118, and is stored in a storage unit 119 implemented by RAMs or hard discs. The reaction container 104 after measuring the light is held by the reaction container carrier 112 and is discarded into a reaction container disposer 117.

The controller 121 may be configured using hardware such as circuit devices implementing the functionalities. Alternatively, the controller 121 may be configured using arithmetic devices such as CPU (Central Processing Unit) executing software implementing the functionalities. The storage unit 119 may be configured using storage devices such as hard discs. The printer 124, the display of the operational computer 118, and the storage unit 119 correspond to the output unit in the embodiment 1.

Embodiment 1

Device Operation

Hereinafter, detailed, process of the controller 121 will be described. The controller 121 detects and removes noises unique to blood clotting reactions from the chronological light intensity data, and calculates the clotting time with high precision. Hereinafter, a noise characteristic of blood clotting reaction will be described first. Then details of the processing sequence will be described.

Blood clotting reaction has a characteristic that it relatively begins rapidly after mixing the sample with the reagent. However, at the initial stage of the reaction, bubbles or other related particles are sometimes dragged into the mixture liquid. It can be assumed that the noise occurring in the light intensity data is caused due to a temporal variation of the measured light intensity when these bubbles or particles pass through the measured region.

In the light of the above-described circumstances, it is anticipated that the noise occurring in the light intensity data has a characteristic that the light intensity varies when the bubbles or the particles enter the measured region and that the light intensity returns back to the original value when the bubbles or the particles exit from the measured region. Therefore, when plotting the light intensity data with the vertical axis as the light intensity and with the horizontal axis as the time of data acquisition, the plotted, shape of the noise portion has an upward or downward convex. In scattered light detection, the amount of scattered light is temporally increased when the light pass through, the bubbles or the particles. Thus the noise shape during reaction has an upward convex.

At the time when the measurement begins, disturbances of fluid flow or bubbles may occur due to impacts of mixing the reagent. In such cases, the light intensity data originally includes noises. Thus the data shape once varies into a recessed shape and then a convex noise appears. These examples of noises will be described later with reference to FIG. 3.

In the light, of these noise characteristics, the controller 121: calculates an approximated curve of the chronological light intensity data; compares the chronological light intensity data with the approximated curve; and detects data departed from the approximated curve only as noise data. Accordingly, it is possible to detect and remove initial noises with convex or recess shapes described above from the chronological light intensity data, thereby highly precisely calculating the blood clotting time.

Figure 2:
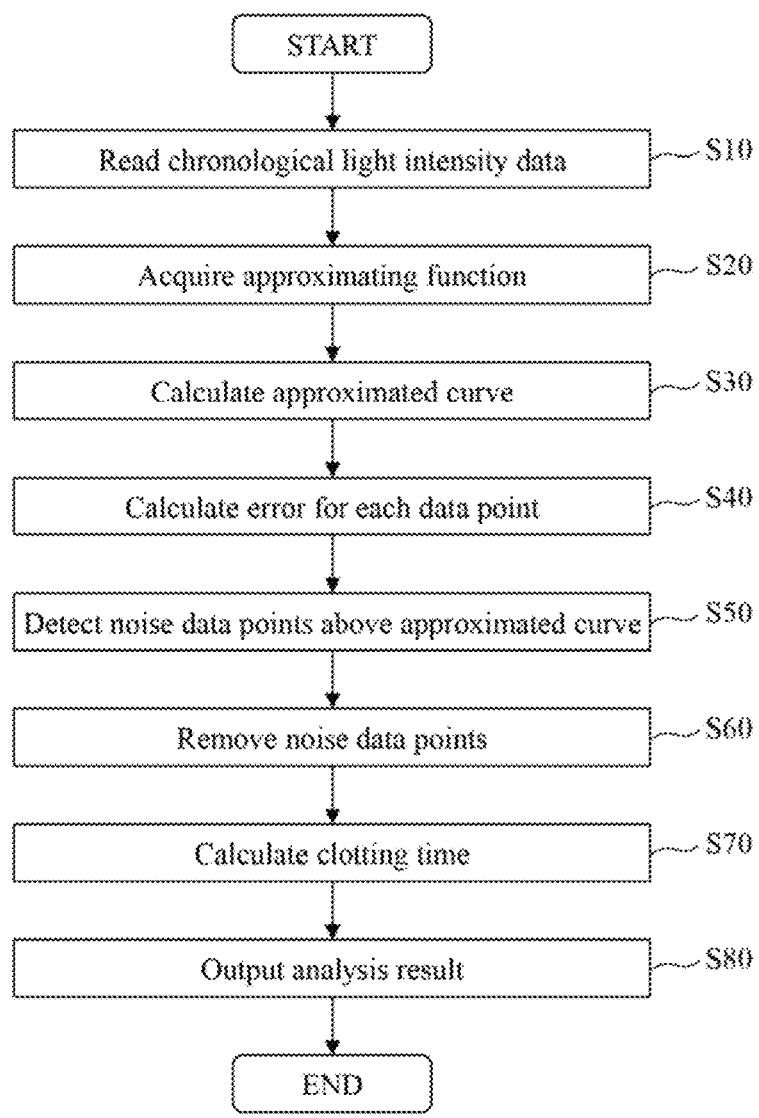
FIG. 2 is a diagram showing a process How in which a controller 121 detects and removes a noise in light intensity data to calculate a blood clotting time.

FIG. 2 is a diagram showing a process flow in which the controller 121 detects and removes a noise in the light intensity data to calculate a blood clotting time. Hereinafter, each step in FIG. 2 will be described.

(FIG. 2: step S10)

Through the A/D converter 122 and through the interface 123, the controller 121 reads, as the chronological light, intensity data, light/electric current conversion data detected by the detector 116 at a predetermined interval. The controller 121 monitors the acquired chronological light intensity data. When the blood clotting reaction stops, the process proceeds to step S20, Commonly known methods may be used as the method for determining whether the clotting reaction has stopped. For example, it can be determined whether the clotting has stopped by methods such as: setting a threshold for the measuring time of the chronological light intensity data; or setting a threshold of newest light intensity or of amount of variation in light intensity.

(FIG. 2: step S20)

The controller 121 selects and acquires, among approximation functions previously stored in the storage unit 119 that approximate temporal variation of light intensity, an optimal approximation function adapted to the combination of the test items and the reagent. For example, the combination of the test, items and the reagent and corresponding approximation function are previously defined, and the optimal approximation function may be automatically selected according to the definition. Logistic function shown in Equation 1, below may be used as the approximation function, for example. In Equation 1, t represents time and y represents light intensity, ymax, yrange, $\alpha1$, and $\alpha2$ are parameters.

$$y = ymax - yrange/(1+\exp(\alpha1(t-\alpha2))) \quad \text{Equation 1}$$

(FIG. 2: step S30)

The controller 121 calculates parameters in the approximation function, so that the difference between the approximated, curve of time-light intensity described by the approximation function selected in step S20 and the actual chronological light intensity data becomes small as far as possible. For example, the controller 121 determines the parameters in the approximation function so that the square error between the chronological light intensity data and the light intensity calculated by the approximation function becomes small as far as possible. For example, least square method may be combined with steepest descent method and with newton method as the method for calculating the parameters. An approximated curve that approximates the light intensity data most precisely will be acquired in this step. In other words, the approximation function stored in the storage unit 119 works as an initial value for calculating the approximated curve indicating the light intensity data.

(FIG. 2: step S40)

The controller 121 calculates, for each point of the chronological light intensity data, the error between the chronological light intensity data and the approximated curve calculated in step S30. The error in this step is not calculated as an absolute value but as a value having positive or negative values. For example, the difference between both of the data is calculated by subtracting the light intensity calculated by the approximated curve from the chronological light intensity data.

(FIG. 2: step S50)

The controller 121 compares the chronological light intensity data with the approximated curve calculated in step S30. The controller 121 detects data points departed from the approximated curve (in scattered light detection, data points above the approximated curve) as noise data points. For example, for each of the data points with positive errors calculated in step S40, the error is compared with a predetermined threshold. If the error is at or above the threshold, the corresponding data point is detected as noise data point. Noises such as convex-shaped noises or recess-shaped noises may be detected in this step.

(FIG. 2: step S60)

The controller 121 removes the noise data points detected in step S50 from the chronological light, intensity data. The noise data points may be actually removed from the chronological light intensity data. Alternatively, a flag indicating whether the data point is a noise may be assigned for each of the data points and the flag data may be stored in the storage unit 119, thereby managing the noise data points.

(FIG. 2: step S70)

The controller 121 calculates the blood clotting time using at least one of: the chronological light intensity data after removing the noise data points acquired in step S60; the approximated curve calculated in step S30. Both of the light intensity data after removing the noise data and the approximated curve provide some indicators about the actual blood clotting reaction. Thus any one of them may be used depending on the purpose of analysis or on the required accuracy. Any commonly known method may be used, as the method for calculating the clotting time. For example, a differential data may be calculated by calculating a difference between adjacent data points of the chronological light intensity data after removing the noise data, and the peak position of the differential data may be calculated as the clotting time.

(FIG. 2: step S80)

The controller 121, outputs to the operational computer 118 and to the printer 124 and stores in the storage unit 119, the information such as: fundamental information such as sample numbers or test items; the chronological light intensity data acquired in step S10; the approximated curve calculated in step S30; the noise data points detected in step S50; or the blood clotting time calculated in step S70.

Figure 3:
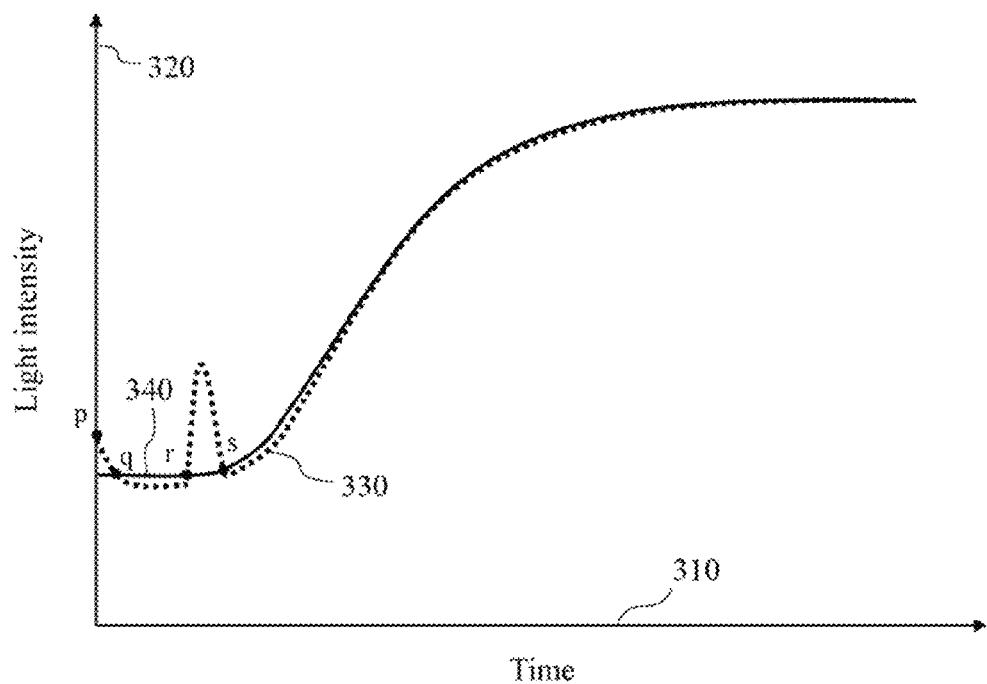
FIG. 3 is a diagram showing a processing image when detecting a noise data point in step S50.

FIG. 3 is a diagram showing a processing image when detecting a noise data point in step S50. The horizontal axis 310 represents the time progress from the start of reaction. The vertical axis 320 represents the light intensity. The dotted curve 330 represents data, points schematically showing the chronological light intensity data. The solid line 340 represents the approximated curve calculated in step S30.

The dotted curve 330 includes a noise data with recessed shape immediately after the start of measurement (dotted line p-q portion). In addition, at the initial stage of reaction, the clotted curve 330 includes a noise data with convex shape due to such as bubbles (dotted line r-s). By comparing the approximated curve 340 with the light intensity data 330, the noise data points departed from, the approximated curve 340 (in FIG. 3, only the noises above the approximated curve 340 are detected) may be detected.

Figure 4:
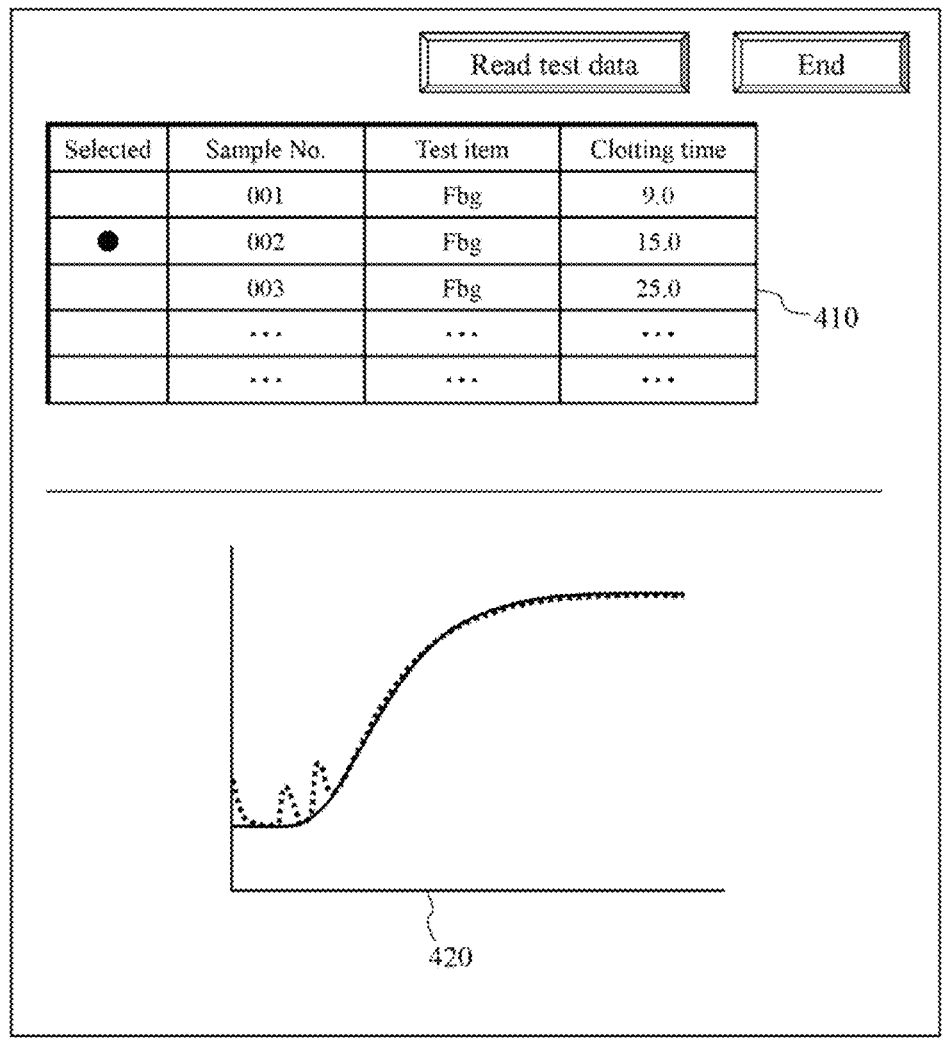
FIG. 4 is a diagram showing an output screen example of an operational computer 118.

FIG. 4 is a diagram showing an output screen example of the operational computer 118. The screen shown in FIG. 4 includes: a fundamental information display area 410 showing fundamental information such as sample numbers, test items, or analysis results (blood clotting time); and a graph display area 420 showing the chronological light intensity data of the selected sample and showing the approximated curve calculated in step S30. The graph display area 420 may display the light intensity data itself measured by the detector 113. Alternatively, the graph display area 420 may display the light intensity data after removing the noise data points. Further, the graph display area 420 may display the equation of the approximation function used in calculating the approximate line.

The controller 121 may store, in the storage unit 119, data such as: the data calculated in the process of FIG. 2; or the light intensity data in progress of removing the noise data points. Further, the controller 121 may display the data regarding the progress of the process on the screen shown in FIG. 4.

Embodiment 1

Modified Example

In the description above, the controller 121 performs the process shown in FIG. 2. However, other functional units may perform the process. For example, software implementing the same process is provided in the operational computer 118, and the computer 118 may perform the process instead of the controller 121. It applies to the embodiments below.

In the description above, the approximation function, the data in progress, or the processed result, are stored in the storage unit 119. However, these data may be stored in other functional units. For example, these data may be stored in a storage unit in the operational computer 118.

In step S20, Equation 1 is used as the approximation function. However, the approximation function which may be used in the present invention is not limited to Equation 1. Various types of growth function with growth curve may be used. The growth function mentioned here is a function that has a shape in which; the amount of variation with respect to time is small at initial stage; the amount of variation is gradually increased; and the amount of variation is decreased again at later stages. Examples of such growth function include logistic function, Gompertz function, or Hill function. Other functions may be used such as: a function in which parts of terms in the above-described growth functions are exponentiated; a function in which a non-linear equation with respect to time is multiplied to or added to the above-described growth functions; or a function in which inputted values of the above-described growth functions are nonlinearly converted by nonlinear equations. Multi-term functions may be used as the nonlinear equations.

In step S50, in order to remove noise data points with upward convex shape, the noise data points above the approximated curve are removed. When analyzing blood clotting reactions according to transmitted light, it is necessary to remove noise data points with downward convex shape. In this case, the data points below the approximated curve are detected as noise data points. The basis on which the data points are removed is the same as that in step S50.

In step S80 and in FIG. 4, the clotting reaction curve indicated by the chronological light intensity data and the approximated curve of step S30 are outputted in the same graph. However, these data may be outputted in different graphs separately. In addition, these data may be outputted with different colors so that the noise data points can be easily distinguished. Alternatively, the shape of data points may be modified.

Embodiment 1

Summary

As discussed thus far, the automated analysis device according to the embodiment 1: calculates the approximated curve of the chronological light intensity data; and compares the chronological light intensity data with the approximated curve, thereby detecting the data above or below the approximated curve only as noise data points. Accordingly; it is possible to detect and remove convex-shaped noises unique to blood clotting reactions or recess-shaped noises at the time starting the measurement. As a result, it is possible to highly precisely calculate the blood clotting time.

Embodiment 2

In an embodiment 2 of the present invention, an operational example for removing noise data points will be described which is different from that of the embodiment 1. The configurations of the automated analysis device are the same as those of the embodiment 1. Thus the difference regarding the operation of the controller 121 will be mainly described.

In the embodiment 2, the controller 121 repeats: a first process for calculating the approximated curve of the chronological light intensity data; a second process for detecting noise data points using the approximated curve; and a third process for removing the noise data points. In general, with respect to data that always includes a certain amount of noise, it is possible to reproduce the original data without noise by calculating an approximated curve once. However, the noise unique to blood clotting reaction occurs at limited positions with asymmetric shapes with respect to increasing direction of data and to decreasing direction of data. Thus it is likely that the precise approximated curve cannot be acquired only by calculating the approximated curve once. Thus in the embodiment 2, the controller 121 repeats the first-third processes to detect and remove noise data points gradually, thereby calculating the precise approximated curve. Accordingly, it can be assumed that the blood clotting time is highly precisely calculated.

Figure 5:
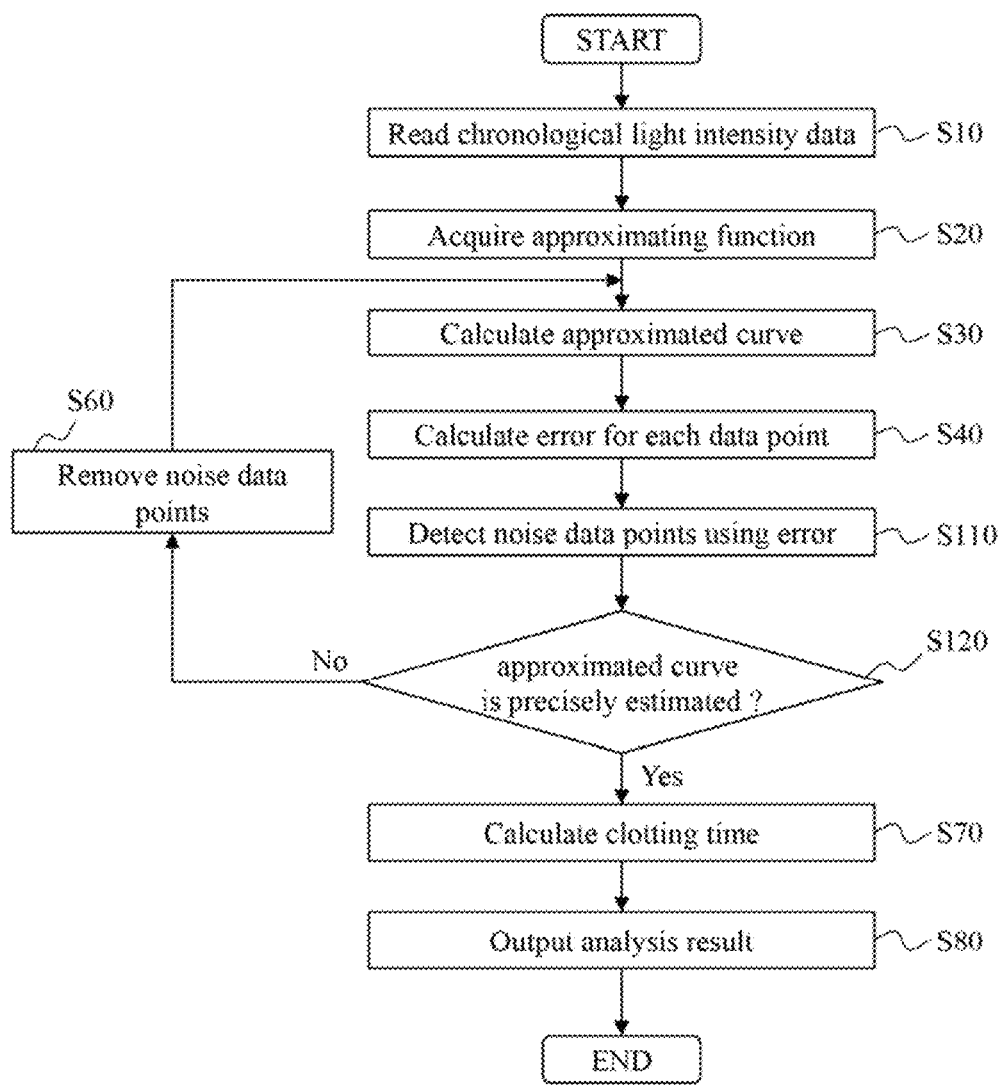
FIG. 5 is a diagram showing a process flow in which the controller 121 calculates a blood clotting time in an embodiment 2.

FIG. 5 is a diagram showing a process flow in which the controller 121 calculates a blood clotting time in the embodiment 2. In the process flow shown in FIG. 5, the same step numbers are assigned for the same steps described in FIG. 2 of the embodiment 1. Namely, steps S10-S40 and steps S60-S80 are same as those of FIG. 2 and thus detailed descriptions are omitted here. In the embodiment 2, steps S110 and S120 are introduced between steps S40 and S70. Step S60 is branched from step S120. The process returns to step S30 after step S60.

(FIG. 5: Step S110)

The controller 121 detects data points that are departed from the approximated curve calculated in step S30. For example, the controller 121: compares a predetermined threshold with the error for each of data points with positive errors calculated in step S40; and detects data points with errors at or above the threshold as noise data points.

(FIG. 5: Step S120)

The controller 121 determines whether the current approximated curve is ideal with respect to the chronological light intensity data. For example, the controller 121: compares the number of noise data points detected in step S110 with a preconfigured threshold; and determines whether the approximated curve is precisely estimated on the basis of whether the number of noise data points is at or above the preconfigured threshold. If the approximated curve is precisely estimated, the process proceeds to step S70. Otherwise the process proceeds to step S60.

Hereinafter, examples of detecting and removing noises in the embodiment 2 will be described using FIGS. 6-8.

Figure 6:
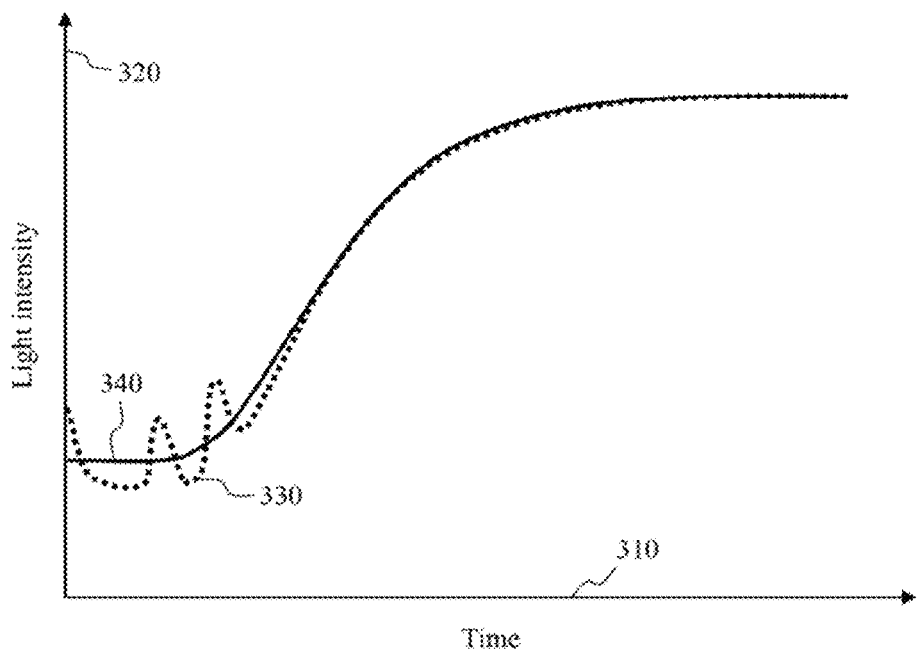
FIG. 6 is a diagram showing a processing image when detecting a noise data point in the embodiment 2.

FIG. 6 is a diagram showing a processing image when detecting a noise data point in the embodiment 2. The reference signs in FIG. 6 represent the same meaning as those in FIG. 3. In FIG. 6, there are noise data points above the approximated curve.

Figure 7:
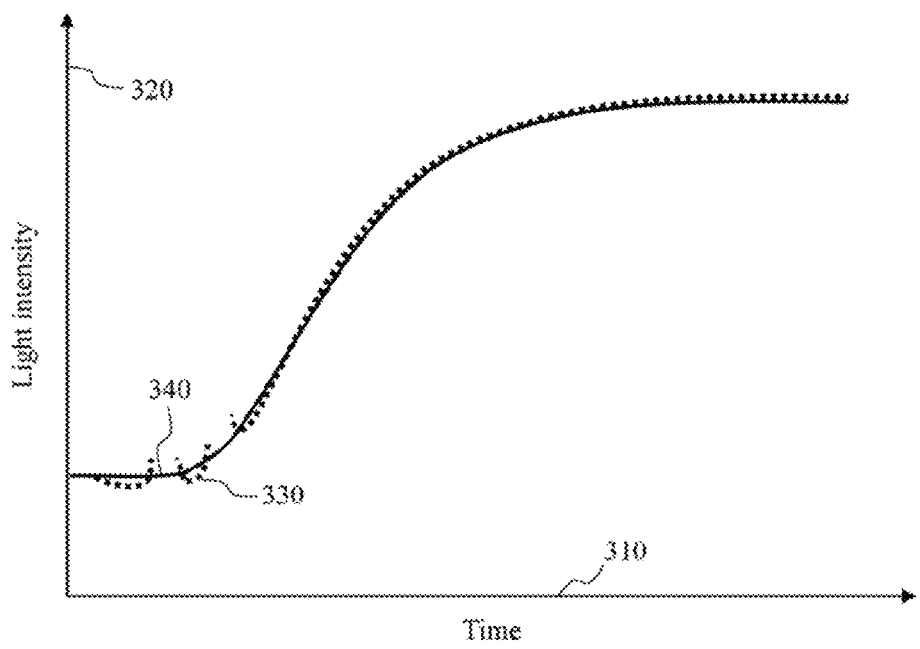
FIG. 7 is a diagram showing a condition after processes of step S40, S110, S120, S60, and S30 are applied.

FIG. 7 is a diagram showing a condition after processes of step S40, S110, S120, S60, and S30 are applied to the chronological light intensity data 330 and to the approximated curve 340 in FIG. 6. In FIG. 7, the noise data points of the chronological light intensity data 330 are removed by step S60. In addition, the approximated curve 340 is updated in the second execution of step S30.

Figure 8:
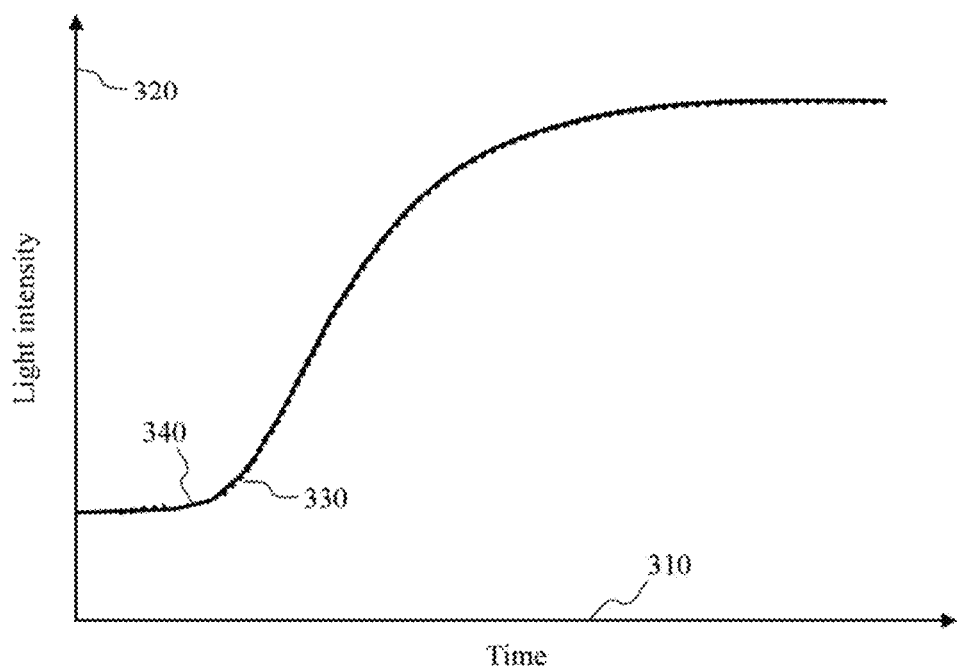
FIG. 8 is a diagram showing a condition after repeating detections and removals of noise data points and calculations of an approximated curve 340.

FIG. 8 is a diagram showing a condition after repeating detections and removals of noise data points and calculations of the approximated carve 340 until it is determined in step S120 that the number of noise data points is at or below the threshold. All noise data points are detected and removed from the chronological light intensity data 330. The approximated curve 340 almost matches with the chronological light intensity data 330 after removing the noise data points.

Comparing FIG. 8 with FIG. 6, the initial rise of waveform and noise potions are removed from the chronological light intensity data 330 by repeating detections and removals of noise data points and calculations the approximated curve. In addition, the approximated curve 340 in FIG. 8 is an ideal approximated curve that interpolates the region where the noise data points are removed from the chronological light intensity data 330.

Embodiment 2

Modified Example

In step S110, in order to remove the noises with upward convex shape, noise data points are detected considering the positive and negative errors, as in the embodiment 1. However, when analyzing blood clotting time according to scattered light, it is necessary to remove noise data points with downward convex shape. Alternatively, both of noise data points above and below the approximated curve may be detected as noise data points. In this case, a threshold may be set with respect to an absolute difference between the approximated curve and the chronological data points. If the absolute error exceeds the threshold, the corresponding data point, may be handled as a noise data point.

In step S120, it is determined whether the approximated curve is precisely estimated by comparing the number of data points with the threshold. However, the basis of determination in step S120 is not limited to it. For example, a threshold may be configured with respect to the proportion of number of noise data points to the total number of the chronological light intensity data points. Alternatively, a threshold may be configured with respect to a standard deviation of the error.

Embodiment 2

Summary

As discussed thus far, the automated analysis device according to the embodiment 2 repeats: a first process for calculating the approximated curve of the chronological light intensity data; a second process for detecting noise data points using the approximated curve; and a third process for removing the noise data points, thereby detecting and removing the noise data points gradually. Accordingly, it is possible to calculate an ideal approximated curve that interpolates the region where the noise data points are removed, thereby highly precisely calculating the blood clotting time.

Embodiment 3

In an embodiment 3 of the present invention, an operational example for removing noise data points will be described which is different from those of the embodiments 1-2. The configurations of the automated analysis device are the same as those of the embodiments 1-2. Hereinafter, the difference regarding the operation of the controller 121 will be mainly described.

In the embodiment 3, the controller 121 configures, using the inputted chronological light intensity data, the threshold in detecting noise data described in the embodiments 1-2. Accordingly, the controller 121 attempts to improve the accuracy for detecting and removing the noise data.

Figure 9:
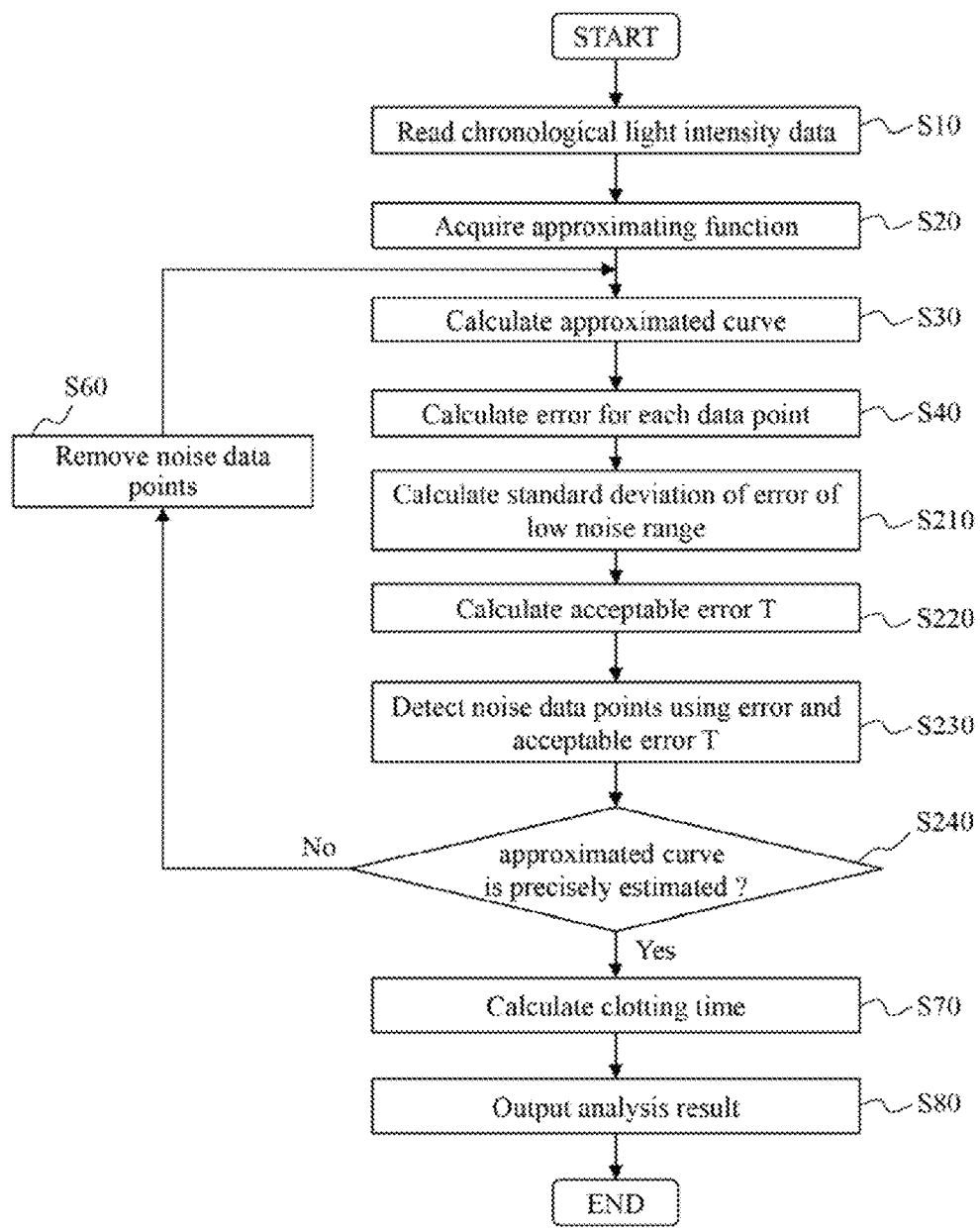
FIG. 9 is a diagram showing a process flow in which the controller 121 calculates a blood clotting time in an embodiment 3.

FIG. 9 is a diagram showing a process flow in which the controller 121 calculates a blood clotting time in the embodiment 3. In the process flow shown in FIG. 9, the same step numbers are assigned for the same steps described in FIG. 2 of the embodiment 1. Namely steps S10-S40 and steps S60-S80 are same as those of FIG. 2 and thus detailed descriptions are omitted here. In the embodiment 3, steps S210-S240 are introduced between steps S40 and S70. Step S60 is branched from step S240. The process returns to step S30 after step S60.

(FIG. 9: Step S210)

The controller 121 selects a subset of the chronological light intensity data as a low noise range, and calculates a standard deviation S of the errors within the subset. The low noise range selected in this step is a range where it is assumed that the chronological light intensity data does not include large noises. For example, in blood clotting reactions, it is likely that large noises occur immediately after the start of reaction. Therefore, the low noise range may be determined by such as: assuming that the reaction start time of the acquired chronological light intensity data is t_start and that the reaction end time is t_end, the center of those times t_middle (t_middle=(t_start+t_end)/2) is calculated; and the data after the time t_middle may be selected as the low noise range.

(FIG. 9: Step S220)

The controller 121 determines an acceptable error T for noise detection using the standard deviation S calculated in step S210. T may be determined according to Equation 2 below, for example. In Equation 2, K represents a predefined constant parameter that adjusts sensitivity for detecting noise data points. For example, if the dispersion of data within the low noise range is a normal distribution, the parameter K=3.0 detects data departed from the approximate line within the low noise range at sensitivity of about 0.3%.

$$T=K*S \quad \text{Equation 2}$$

(FIG. 9: Step S230)

The controller 121 detects data points departed from the approximated curve using the acceptable error T calculated in step S220. For example, for each of the data points with a positive error calculated in step S40, the controller 121 compares the error of each data point calculated in step S40 with the acceptable error T, and detects data points with errors at or above the threshold as noise data points.

(FIG. 9: Step S240)

The controller 121 determines whether the current approximated curve is ideal with respect to the chronological light intensity data. For example, the controller 121: compares the number of noise data points detected in step S230 with a preconfigured threshold; and determines whether the approximated curve is precisely estimated on the basis of whether the number of noise data points is at or above the threshold. If the approximated curve is precisely estimated, the process proceeds to step S70. Otherwise the process proceeds to step S60.

Embodiment 3

Advantageous Effect

In general, the chronological light intensity data includes the three components below. (1) original chronological variations of blood clotting reaction, (2) micro noises that are globally derived from measuring environments, (3) local noises that are derived from bubbies and particles when stirring.

The noise of (2) is a noise derived from various environments such as: a noise derived from hardware such as the detector 116 or the A/D converter 122; or a noise derived from the reactive solution in the reaction container. The noise of (2) is typically symmetrical with respect to the data increasing and decreasing directions and its amplitude is small. Thus it is possible to, by calculating the approximated curve, reproduce the original data in which the noise is removed.

On the other hand, the noise of (3) is asymmetric with respect to the data increasing and decreasing directions and its amplitude is large. Thus it is not possible to reproduce the original data in which the noise is removed even if the approximated curve is calculated. Therefore, it can be expected to acquire a highly precise approximated curve by removing the noise of (3) before calculating the approximated curve. However, when using the noise data point detection described in the embodiments 1-2, both of the noises (2) and (3) may be detected depending on the threshold. Thus the data points may be excessively removed or the noise may not be removed sufficiently.

Thus in the embodiment 3, step S220 configures the threshold according to the chronological light intensity data at the later stage in which it is not likely that the noise of (3) is included. The noise Is detected using this threshold. This threshold is configured according to the variation of (2), which corresponds to a steady noise component. By configuring an appropriate value of K (e.g. 3.0) in Equation 2, it is possible to detect data points related to the noise of (3) only. A specific example will be described using FIG. 10.

Figure 10:
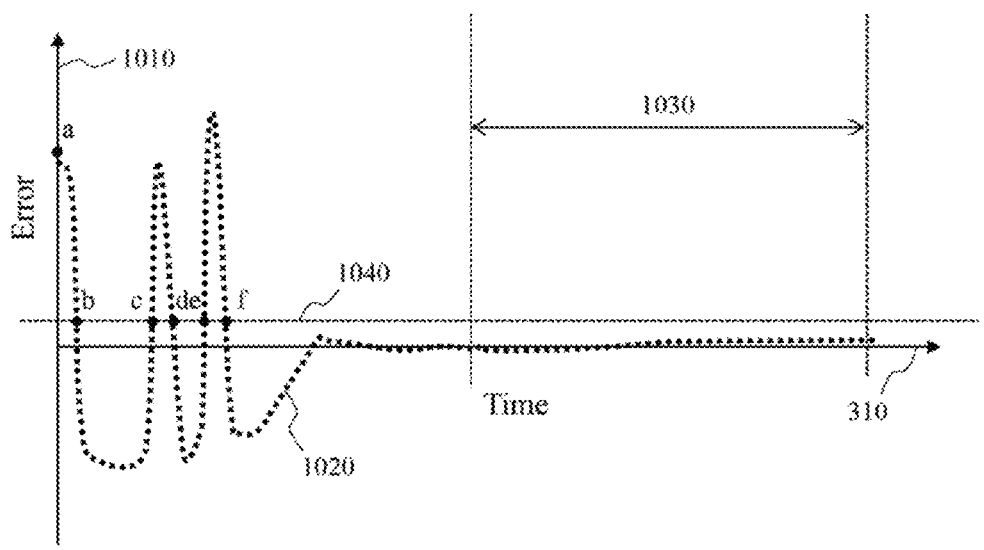
FIG. 10 is a diagram in which a difference between chronological light intensity data 330 and the approximated curve 340 shown in FIG. 6 is calculated and is plotted.

FIG. 10 is a diagram, in which a difference between the chronological light intensity data 330 and the approximated curve 340 shown in FIG. 6 is calculated and is plotted. The horizontal axis 310 represents the same meaning as that of FIG. 3. The vertical axis 1010 represents an error between the chronological light intensity data 330 and the approximated curve 340. The dotted curve 1020 plots the error between the chronological light intensity data 330 and the approximated curve 340. The reference sign 1030 represents a low noise range configured in step S210. The reference sign 1040 represents the threshold T configured in step S220.

In FIG. 10, the dotted curve a-b, the dotted curve c-d, and the dotted curve e-f are chronological data points that are determined as noises by comparing with the threshold T. By configuring the threshold T according to light intensity data at the later stage, it is possible to detect local noises only that are derived from such as bubbles or particles.

The automated analysis device according to the embodiment 3 not only detects the local noises as described, with FIG. 10 but also improves the accuracy for determining the end of repetition. This advantageous effect will be described below.

At the initial stage of repetition, the noise of (3) is not completely removed. Thus the approximated curve is not precisely calculated and the data point is not precisely approximated in some cases even within the low noise range. In this case, the threshold configured on the basis of the standard deviation of errors within the low noise range does not precisely reflect the variations of noise (2). Thus the threshold only detects data points with large amplitudes among the noises (3). However, as the repetition proceeds and as the noise (3) is removed, the approximated curve gradually approaches the original data after the noise is removed. At this time, while the noise (2) still remains, the threshold configured by using the low noise range gradually approaches an optical threshold that is capable of removing the noise (3) only. By determining the threshold for determining the end of repetition using the method of the embodiment 3, it is possible to appropriately determine the end of repetition without excessively removing data points or without leaving the noise. A specific example will be described using FIG. 11.

Figure 11:
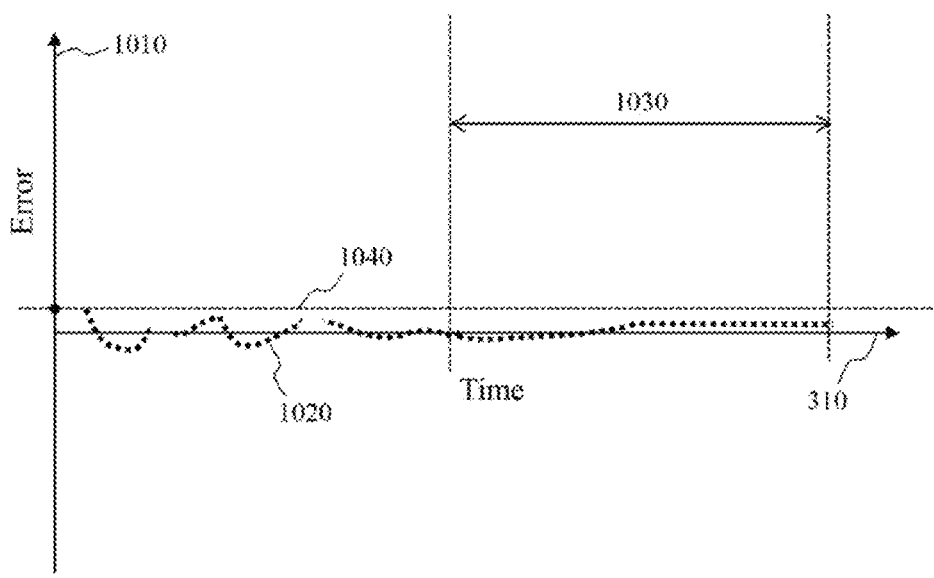

FIG. 11 is a diagram showing a condition after repeating detections and removals of noise data points and calculations of an approximated curve 340 with respect to the error between the chronological light intensity data 330 and the approximated curve 340 in FIG. 10. The reference signs in FIG. 11 represent the same meanings as those of FIG. 10.

At the initial stage of repetition (the state of FIG. 10), the initial portion of reaction in the chronological light intensity data 330 includes the noise of (3), and there are a lot of data points above the threshold T. At the later stage of repetition (the state of FIG. 11), the noise (3) is removed and the approximated curve reproduces the original chronological light intensity data in which the noise is removed. Thus the error variations at the initial stage are equivalent to the error variations at the later stage. At this time, the threshold 1040 precisely reflects the variation of noise (2). Therefore, by determining whether the noise (3) exists using this threshold, it is possible to appropriately determine the end of repetition without excessively removing data points or without leaving noises. This method for determining the end of repetition may be used in the embodiment 2.

Embodiment 3

Modified Example

In step S210, data after the time t_middle of the acquired chronological light intensity data is selected as the low noise range. However, the low noise range may be selected on other basis. For example, a threshold may be configured with respect to the light intensity value of the acquired chronological light intensity data, and data with light intensity value at or above the threshold may be selected. Alternatively, a plurality of low noise ranges is configured; standard deviations of errors between the chronological data and the approximated curve are calculated for each of the low noise ranges; one of the standard deviations may be selected as a standard deviation of noise of the low noise range, or a standard deviation of noise of the low noise range may be calculated using the plurality of standard deviations. In addition, the method for selecting the low noise range may be changed for each of the test items. Further, the method for selecting the low noise range may be changed for each of the repetition.

In step S230, in order to remove the noises with upward convex shape, noise data points are detected considering the positive and negative errors, as in the embodiment 1. However, when analyzing blood clotting time according to scattered light, it is necessary to remove noise data points with downward convex shape. Alternatively, both of noise data points above and below the approximated curve may be detected as noise data points. In this case, a threshold may be set with respect to an absolute difference between the approximated curve and the chronological data points. If the absolute error exceeds the threshold, the corresponding data point may be handled as a noise data point.

In step S240, it is determined whether the approximated curve is precisely estimated by comparing the number of data points with the threshold. However, the basis of determination in step S240 is not limited to it. For example, a threshold may be configured with respect to the proportion of number of noise data points to the total number of the chronological light intensity data points. Alternatively, a threshold may be configured with respect to a standard deviation of the error. In addition, those thresholds may be configured according to the standard deviation calculated in step S210.

Embodiment 3

Summary

As discussed thus far, the automated analysis device according to the embodiment 3 improves the accuracy for determining the end of repetition by configuring the threshold according to the chronological light intensity data at the later stage. In addition, as described with FIG. 10, it is possible to remove local noises only while leaving steady micro noises.

The present invention is not limited to the embodiments, and various modified examples are included. The embodiments are described in detail to describe the present invention in an easily understood manner, and the embodiments are not necessarily limited to the embodiments that include all configurations described above. Part of the configuration of an embodiment can be replaced by the configuration of another embodiment. The configuration of an embodiment can be added to the configuration of another embodiment. Addition, deletion, and replacement of other configurations are also possible for part of the configurations of the embodiments.

REFERENCE SIGNS LIST

101: sample dispenser
102: sample disc
103: sample container
104: reaction container
105: sample syringe pump
106: reagent dispenser
107: reagent disc
108: reagent container
109: reagent heater
111: reagent container stock
112: reagent container carrier
113: detector
114: reagent container locator
115: light source
116: detector
117: reagent container disposer
118: operational computer
119: storage unit
120: input unit
121: controller
122: A/D converter
123: interface

The invention claimed is:

1. An automated analysis device that analyzes a blood clotting reaction comprising:
a reaction container for mixing a sample with a reagent to cause a reaction;
a measuring unit that irradiates light onto a reaction solution in the reaction container and that measures a scattered light intensity or a transmitted light intensity;
a controller that processes chronological light intensity data measured by the measuring unit;
a storage unit that stores one or more of approximation functions approximating a chronological variation of the light intensity data; and
an output unit that outputs a processed result of the controller,
wherein the controller selects one of the approximation functions stored in the storage unit, wherein the controller is programmed to perform: a first process calculating an approximated curve representing a chronological variation of the light intensity data using the selected approximation function; a second process detecting, using the approximated curve, an abnormal data point included in the light intensity data; and a third process removing the abnormal data point from the light intensity data,
wherein the controller is configured to analyze the blood clotting reaction using at least one of the light intensity data and the approximated curve,
and wherein when detecting the abnormal data point in the third process, the controller is configured to detects, as the abnormal data point, only one of a data point in the light intensity data having a light intensity value larger than that of the approximated curve and a data point in the light intensity data having a light intensity value smaller than that of the approximated curve.

2. The automated analysis device according to claim 1, wherein the measuring unit detects the scattered light intensity, and wherein the controller is configured to detects, as the abnormal data point, a data point in the light intensity data having a light intensity value larger than that of the approximated curve.

3. The automated analysis device according to claim 1, wherein the measuring unit detects the transmitted light intensity, and wherein the controller is configured to detects, as the abnormal data point, a data point in the light intensity data having a light intensity value smaller than that of the approximated curve.

4. The automated analysis device according to claim 1, wherein the controller repeats the first process, the second process, and the third process for at least one or more times, and wherein the controller is configured to analyze the blood clotting reaction using at least one of the light intensity data and the approximated curve at a time when a predetermined convergence condition is satisfied.

5. The automated analysis device according to claim 1, wherein the controller selects a subset from the light intensity data, and wherein the controller is configured to detects the abnormal data point included in the light intensity data using differences between the light intensity data and the approximated curve for each of data points and using a standard deviation of differences between the subset and the approximated curve for each of data points.

6. The automated analysis device according to claim 4, wherein the controller selects a subset from the light intensity data, and wherein the controller is configured to determine whether the convergence condition is satisfied using a standard deviation of differences between the subset and the approximated curve for each of data points.

7. The automated analysis device according to claim 5, wherein the controller uses, as the subset, the light intensity data after a predetermined time has passed from when the measuring unit starts measuring the light intensity data.

8. An automated analysis device that analyzes a blood clotting reaction comprising:

a reaction container for mixing a sample with a reagent to cause a reaction;

a measuring unit that irradiates light onto a reaction solution in the reaction container and that measures a scattered light intensity or a transmitted light intensity;

a controller that processes chronological light intensity data measured by the measuring unit; a storage unit that stores one or more of approximation functions approximating a chronological variation of the light intensity data; and an output unit that outputs a processed result of the controller, wherein the controller selects one of the approximation functions stored in the storage unit, wherein the controller is programmed to perform: a first process calculating an approximated curve representing a chronological variation of the light intensity data using the selected approximation function; a second process detecting, using the approximated curve, an abnormal data point included in the light intensity data; and a third process removing the abnormal data point from the light intensity data, wherein the controller repeats the first process, the second process, and the third process for at least one or more times, and wherein the controller is configured to analyze the blood clotting reaction using at least one of the light intensity data and the approximated curve with a state using a predetermined convergence condition.

9. The automated analysis device according to claim 1, wherein the controller is programmed to calculate the approximated curve by varying a coefficient of the approximation function so that a squared error between the approximation function and the light intensity data becomes smallest.

10. The automated analysis device according to claim 1, wherein the approximation function is a function having a first region in which an amount of variation of light intensity with respect to time becomes gradually large and a second region in which an amount of variation of light intensity with respect to time is smaller than that of the first region at a time after the first region.

11. The automated analysis device according to claim 1, wherein the controller is programmed to calculate a clotting time of the blood clotting reactions using at least one of the light intensity data and the approximated curve.

12. The automated analysis device according to claim 1, wherein the output unit outputs one or more of:
(1) the light intensity data using time as a first axis and using light intensity as a second axis;
(2) the approximated curve using time as a first axis and using light intensity as a second axis;
(3) a result of the analysis; and
(4) an equation of the approximation function.

13. An automated analysis method for analyzing a blood clotting reaction comprising:

a measuring step of irradiating light onto a reaction solution in a reaction container for mixing a sample with a reagent to cause a reaction and of measuring a scattered light intensity or a transmitted light intensity;

a control step of processing chronological light intensity data measured in the measuring step; and an output step of outputting a processed result in the control step, wherein the control step includes a step of selecting and reading an approximation function approximating a chronological variation of the light intensity data from a storage unit that stores one or more of the approximation functions, wherein the control step includes a step of performing: a first process calculating an approximated curve representing a chronological variation of the light intensity data using the selected approximation function; a second process detecting, using the approximated curve, an abnormal data point included in the light intensity data; and a third process removing the abnormal data point from the light intensity data, wherein the control step includes a step of analyzing the blood clotting reaction using at least one of the light intensity data and the approximated curve, and wherein when detecting the abnormal data point in the third process, only one of a data point in the light intensity data having a light, intensity value larger than that of the approximated curve and a data point in the light intensity data having a light intensity value smaller than that of the approximated curve is detected as the abnormal data point.

\* \* \* \* \*